United States Patent [19]
Bodmer

[11] 3,955,403
[45] May 11, 1976

[54] METHOD OF AND APPARATUS FOR DETERMINING THE PURITY OF BOILER FEEDWATER

[75] Inventor: Maurice Bodmer, Nussbaumen, Switzerland

[73] Assignee: BBC Brown Boveri & Company Limited, Baden, Switzerland

[22] Filed: Aug. 16, 1974

[21] Appl. No.: 498,204

[30] Foreign Application Priority Data
Aug. 24, 1973 Switzerland.................. 12174/73

[52] U.S. Cl................................. 73/61 R; 159/30
[51] Int. Cl.²..................... G01N 27/00; B01D 1/02
[58] Field of Search............. 73/61 R, 61.1 R, 29; 324/65 R; 159/30; 23/274, 275

[56] References Cited
UNITED STATES PATENTS

| | | | |
|---|---|---|---|
| 3,205,045 | 9/1965 | Von Lossberg | 324/65 R X |
| 3,430,483 | 3/1969 | Clawson et al. | 73/29 |
| 3,542,113 | 11/1970 | Mostofin et al. | 159/30 |

Primary Examiner—Richard C. Queisser
Assistant Examiner—Joseph W. Roskos
Attorney, Agent, or Firm—Pierce, Scheffler & Parker

[57] ABSTRACT

Purity of boiler feedwater being the effluent of a condensate polishing plant in a steam power station is determined by a method in which some of the effluent is used as feedwater for an auxiliary boiler. The blow down from this boiler, which uses a much higher evaporation ratio than the main steam generator, is sampled and provides — by measurement of its conductivity — an indirect determination of condensate purity. With a condensate polishing plant consisting of more than two, e.g. three filter units, and with one filter unit shut down for regeneration one uses as feedwater for the auxiliary boiler effluent of that one of the other two filters which is nearest to its exhaustion state, i.e. the filter which has been in operation the longest at this time.

12 Claims, 1 Drawing Figure

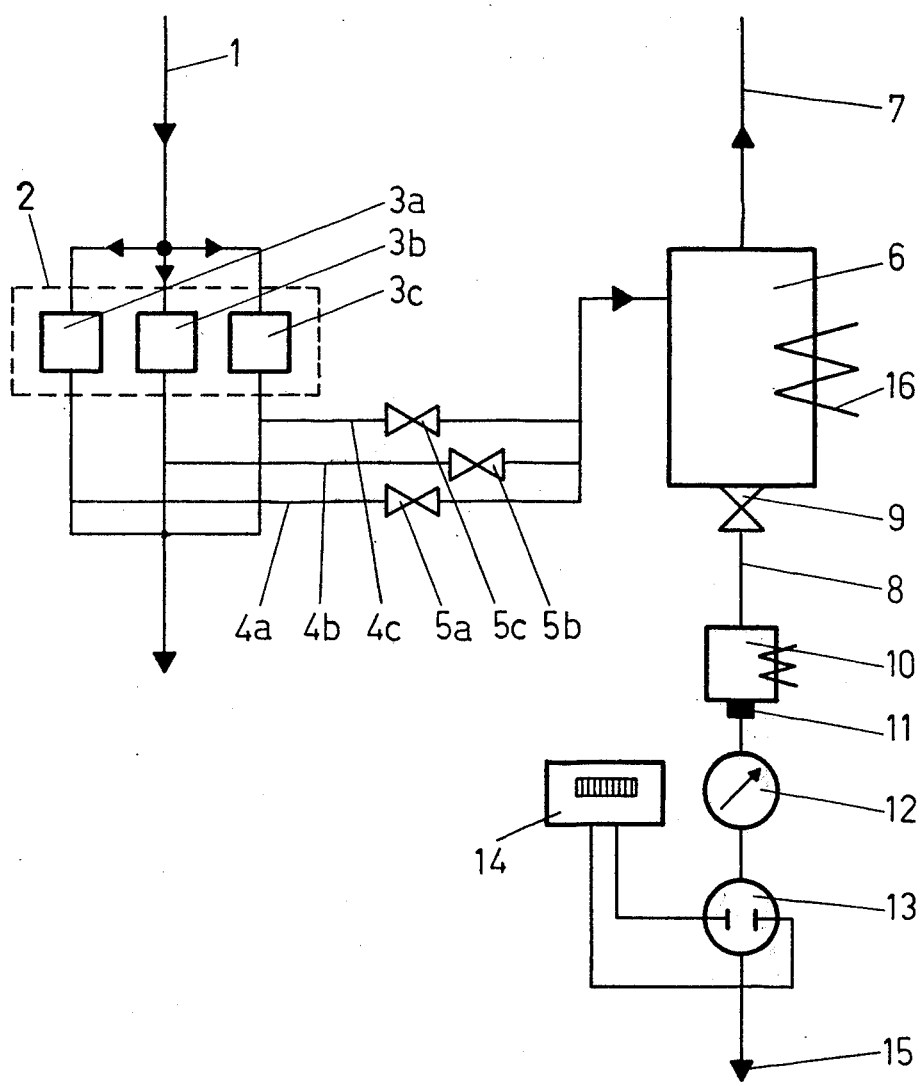

METHOD OF AND APPARATUS FOR DETERMINING THE PURITY OF BOILER FEEDWATER

The present invention relates to an improved method of and apparatus for determining the purity of boiler feedwater occurring as condensate in a steam power station and treated in a condensate polishing plant.

Measurement of electrical conductivity is known as a means of measuring the mineral content of treated feedwater.

Of particular importance is a precise knowledge of the amount of dissolved solids in the feedwater of boiling water reactor plants. The conductivity of such feedwater after the condensate polishing plant is that of extremely pure water, amounting to only some 0.06 $\mu$mho/cm at 25°C; it is therefore very difficult to measure it exactly. The maximum permissible mineral content of the reactor water corresponds to a conductivity of some 1.0 $\mu$mho/cm. The extent to which this water is usually thickened, i.e. the degree to which the dissolved salts are concentrated through evaporation, is expressed in terms of the concentration factor, and is about 100. According to the rule:

$$\Delta L_S = L_{S_{ef}} - L_{W_{th}} = \frac{L_R - L_{W_{th}}}{E}$$

in which $\Delta L_S$ = Conductivity of impurities in feedwater
$L_{S_{ef}}$ = Conductivity of feedwater
$L_{W_{th}}$ = Theoretical conductivity of technically pure water
$L_R$ = Maximum permissible conductivity of reactor water
$E$ = Concentration factor the conductivity of the feedwater must not exceed some 0.07 $\mu$mho/cm. The difference between 0.06 and 0.07 $\mu$mho/cm is scarcely detectable, because direct measurement of conductivity using modern measuring instruments incorporates an error of about ± 0.01 $\mu$mho/cm, despite thermostatic control of the measuring fluid. Hitherto, the increase in conductivity of feedwater has been measured indirectly by way of the slow, measurable rise in the conductivity of the reactor water. With this method it is often not recognized in time that the filters of the condensate polishing plant are exhausted, and there is therefore a serious danger that salts pass into the reactor.

The object of the invention is to determine more reliably the conductivity of feedwater in order to detect rapidly and exactly even small increases in its mineral content.

This object is achieved in that a small quantity of feedwater is drawn off after the condensate polishing plant, passed to an auxiliary steam generator where it is concentrated by evaporation, port of the concentrated boiler water is blown down and the electrical conductivity of this blown down water is measured.

It is preferable to concentrate the feedwater in such a way that the concentration of dissolved salts in the boiler water is 1000 times that in the feedwater.

It is further recommended that the auxiliary boiler should be "blown down" continuously.

The method allows completely straightforward, accurate detection of even a slight increase in the mineral content of the feedwater, using conventional measuring instruments.

An important advantage is the speed at which the measured values are available, owing to the small quantity of feedwater which has to be thickened.

The method also presents the possibility of revealing cooling-water leakage in the condenser, which has hitherto been difficult to detect by means of conductivity measurements.

If the temperature of the blowdown water is regulated thermostatically, the results of measuring conductivity can be evaluated quantitatively in such a way that they can be used as parameters for regulating and supervising the condensate polishing plant.

Apparatus for implementing the method comprises at least one extraction line branching off after the polishing plant and leading to an auxiliary steam generator, and a blowdown line passing from this steam generator and incorporating a blowdown valve, a cooler with thermostat, a flowmeter and a measuring device having connected to it a means of recording.

The method benefits from the now customary practice whereby in a boiling water reactor plant the gland sealing system of the turbine plant is operated with non-active steam produced from polished condensate.

An example of the invention is shown schematically in the drawing.

The drawing, which shows a part of the heat flow diagram of a steam power station, does not include such components which are not essential to the invention, but are mentioned in the description, such as condenser and feedheater plant and the gland sealing system.

The condensate line 1 leads from the condenser plant to the feedheating system of a boiling water reactor installation. The condensate polishing plant 2 incorporates filters 3a, 3b and 3c, which are connected in parallel and can be mixed-bed filters or precoat filters with pulverized ion exchangers.

The extraction lines 4a, 4b and 4c contain corresponding shutoff valves 5a, 5b and 5c. The assumption is made that of the considered filters the ion exchange resins of filter 3a will be exhausted first because at the considered time they have been in operation the longest since last being regenerated. With valve 5a open, feedwater passes along extraction line 4a to auxiliary steam generator 6. Valves 5b and 5c are closed and extraction lines 4b and 4c are out of operation.

The auxiliary steam generator 6 is a natural-circulation or a controlled circulation boiler heated with active primary steam 16 and produces some 5000 kg of non-active steam per hour which is fed to the turbine gland sealing system by way of steam line 7. Owing to evaporation of the feedwater the concentration of dissolved salts in the boiler water, by which is meant the feedwater present in the auxiliary steam generator, is raised to e.g. 1000 times that of the feedwater. When the prescribed concentration has been reached, mineral-laden boiler water, termed blowdown water, is continuously drained from auxiliary steam generator 6 via blowdown valve 9 into blowdown line 8. The continuous flow rate of blowdown water, the blowdown rate, is regulated in a ratio of 1 : 1000 with respect to the incoming feedwater flow rate by means of a control device, not shown, such as flow-measuring orifice.

The electrical conductivity of this blowdown water is measured when steady conditions, which are essential for measurement, have been achieved in the auxiliary steam generator 6. This steady condition, which depends among other things on supplying feedwater to the steam generator for a sufficiently long time, on the output and liquid content of the steam generator and on the blowdown rate, is reached quite quickly owing to the small size of the natural-circulation boiler.

On passing through the cooler 10, in which the blowdown water is cooled to the temperature necessary for measurement, and a thermostat 11 controls the temperature at 25°C, for example, the continuous flow, in the present case some 5 kg/h, is monitored with flowmeter 12. Measurement, together with display and recording of the conductivity by means of measuring device 13 or recording device 14, then follows in known manner. Samples are taken at regular intervals from discharge 15 of blowdown line 8 for conventional analysis of the boiler water.

Because the feedwater is concentrated by a factor of about a thousand in auxiliary steam generator 6, even a very small increase in the mineral content, and hence the conductivity of the condensate, can be detected extremely accurately in accordance with the rule stated in the general description. Since the blowdown water is drained continuously from the steam generator and the required measuring temperature is held constant by means of a thermostatic control system, the absolute measured values displayed can be evaluated quantitatively and may be used as control parameters.

Recording device 14 contains means, not shown, for initiating an alarm when the conductivity approaches a prescribed maximum value, and also means for automatically shutting down filter 3a when this maximum value is reached, this value being equivalent to exhaustion of the ion exchangers. If the filter 3a in question is shut down, auxiliary steam generator 6 will in turn be fed with the effluent of that filter 3b or 3c which has been in operation the longest at this time. In the meantime the ion exchangers of filter 3a will be regenerated if it is a mixed-bed filter, or coated with fresh resin in the case of a precoat filter.

If the condensate is contaminated by the ingress of raw water, as may occur in the event of leaks in the condenser plant, the subsequent rise in the mineral content of the condensate will have the effect of increasing the loading on the ion-exchange resins, a fact which will become evident only as a result of the thousandfold concentration of the feedwater. On the recorded conductivity curve, the rise in conductivity in relation to time corresponds to the increasing loading on the exchange resins.

The method differs from similar methods in that the results of measuring the conductivity of water taken from a plant component are used to control not this component but quite another system, the condensate polishing plant in the example described.

The concentration factor and blowdown employed in the method can of course be chosen as desired. Nevertheless, the values given in the example are probably the most suitable.

Equally, the method and the apparatus are applicable not only in boiling water reactor plants, but anywhere that very exacting demands are imposed on water quality, in which case the auxiliary steam generator should preferably be a natural-circulation boiler with continuous blowdown.

I claim:

1. The method of determining the purity of boiler feedwater occurring as condensate in a steam power station and treated in a condensate polishing plant with at least two filter units for removal of dissolved mineral salts therein which comprises the steps of:
   drawing off feedwater from the discharge side of the condensate polishing plant,
   concentrating the drawn-off polished condensate to a steady-state condition by partial evaporation of the same in an auxiliary boiler,
   blowing down the concentrated salt-enriched boiler water at a rate which is low in relation to the rate of steam production in the auxiliary boiler, and
   measuring the electrical conductivity of the blown down water to determine the mineral content thereof.

2. The method as defined in claim 1 wherein during the feedwater concentration step the concentration of dissolved minerals in the volume of boiler water being evaporated is increased to about a 1,000 times that of the mineral content of the condensate blown down from the discharge side of the condensate polishing plant.

3. The method as defined in claim 1 wherein the concentrated salt-enriched boiler water is blown down in a continuous flow.

4. The method as defined in claim 1 and which includes the further step of subjecting the blown down concentrated salt-enriched boiler water to a thermostatic temperature control in advance of measuring its electrical conductivity.

5. The method as defined in claim 1 and which includes the further step of utilizing the measured electrical conductivity of the blown down concentrated salt-enriched boiler water as a control parameter for automatic shut-down of the condensate polishing plant.

6. The method as defined in claim 1 and which includes the further step of utilizing the measured electrical conductivity of the blown down concentrated salt-enriched boiler water as a control parameter for regeneration of a filter unit of the condensate polishing plant.

7. The method as defined in claim 1 and which includes the further step of putting that portion of the drawn-off polished condensate which is evaporated in said auxiliary boiler in the form of non-active steam to a useful purpose in said steam power station such as by feeding said steam to the gland sealing system of the steam turbine component of said power station.

8. The method as defined in claim 1 and which includes, for a steam power station having a condensate polishing plant provided with more than two filter units, and with one filter unit shut down for regeneration, the step of using as feedwater for the auxiliary boiler effluent of that one of the remaining filters which has been in operation the longest at this time and is thus the one which is nearest to its exhaustion state.

9. Apparatus for determining the purity of boiler feedwater occurring as condensate in a steam power station and treated in a condensate polishing plant for removal of dissolved mineral salts therein which comprises at least one extraction line connected to the discharge side of said condensate polishing plant for drawing off polished condensate, an auxiliary boiler fed with said polished condensate and partially evaporating said polished condensate to a steady state condition thereby producing a steady state volume of concentrated salt-enriched boiler water, a blow down line from said auxiliary boiler for the concentrated salt-enriched blow down produced in said auxiliary boiler, valve means in said blow down line for controlling the rate at which the concentrated salt-enriched boiler water is blown down, a thermostatically controlled cooling device located in said blow down line for maintaining the blown down concentrated salt-enriched boiler water at a constant temperature, and means for determining the electrical conductivity of the concentrated blown down saltenriched boiler water following discharge from said cooling device thereby to determine the mineral content thereof.

10. Apparatus as defined in claim 9 wherein a flowmeter is also incorporated into said drain line.

11. Apparatus as defined in claim 9 and which further includes a steam take-off line from said auxiliary boiler for conveying the evaporated portion of said polished condensate to the gland sealing system of the steam turbine component of said power station.

12. Apparatus as defined in claim 9 wherein said condensate polishing plant includes a plurality of filter units, an extraction line leading to said auxiliary boiler being provided at the discharge side of each said filter unit, and valve means included in each of said extraction lines for selecting the effluent from the filter unit which is supplied to said auxiliary boiler.

* * * * *